US012782337B2

(12) United States Patent
Sun

(10) Patent No.: US 12,782,337 B2
(45) **Date of Patent: *Nov. 3, 2026**

(54) METHOD AND DEVICE FOR AUTOMATICALLY TRACKING URINE

(71) Applicant: Shanghai Kohler Electronics, Ltd., Shanghai (CN)

(72) Inventor: Qintao Sun, Beijing (CN)

(73) Assignee: Shanghai Kohler Electronics, Ltd., Shanghai (CN)

( * ) Notice: Subject to any disclaimer, the term of this patent is extended or adjusted under 35 U.S.C. 154(b) by 347 days.

This patent is subject to a terminal disclaimer.

(21) Appl. No.: 18/403,577

(22) Filed: Jan. 3, 2024

(65) Prior Publication Data

US 2024/0133866 A1 Apr. 25, 2024
US 2024/0230623 A9 Jul. 11, 2024

Related U.S. Application Data

(63) Continuation of application No. 17/402,184, filed on Aug. 13, 2021, now Pat. No. 11,913,937, which is a (Continued)

(30) Foreign Application Priority Data

Mar. 13, 2018 (CN) ......................... 201810205162.7

(51) Int. Cl.
*G01N 33/493* (2006.01)
*A61B 5/20* (2006.01)
(Continued)

(52) U.S. Cl.
CPC ........... *G01N 33/493* (2013.01); *A61B 5/207* (2013.01); *A61B 10/007* (2013.01); *E03D 11/13* (2013.01); *G16H 80/00* (2018.01)

(58) Field of Classification Search
CPC .... G01N 33/493; A61B 5/207; A61B 10/007; G16H 80/00; E03D 11/13
(Continued)

(56) References Cited

U.S. PATENT DOCUMENTS 10,383,606 B1 8/2019 Mccord et al.
10,731,326 B2 8/2020 Qin et al.
(Continued)

FOREIGN PATENT DOCUMENTS

CN 103186230 A 7/2013
CN 104331903 A 2/2015
(Continued)

OTHER PUBLICATIONS

KIsomura Atsushi) Estimation method of urinary vol. and defecation properties based on visual volume intersection method using multi-view cameras; Summary of master's thesis, School of Information Science and Technology, Aichi Prefectural University, 2015; 2 pgs.

(Continued)

*Primary Examiner* — Huyen D Le
(74) *Attorney, Agent, or Firm* — Lempia Summerfield Katz LLC

(57) ABSTRACT

A method of automatically tracking urine in a toilet includes creating a background image of an interior of a toilet bowl using an image sensor, wherein the background image shows the interior of the toilet bowl. The method also includes acquiring an image of the interior of the toilet bowl using the image sensor, wherein the acquired image shows urine and a collecting and tracking member in the interior of the toilet bowl. The method further includes producing a difference image that shows a difference between the acquired image and the background image, and processing the difference image to identify a location of the urine and
(Continued)

the collecting and tracking member, and moving the collecting and tracking member to the identified location of the urine.

17 Claims, 5 Drawing Sheets

Related U.S. Application Data continuation of application No. 16/299,773, filed on Mar. 12, 2019, now Pat. No. 11,119,091.

(51) Int. Cl.
*A61B 10/00* (2006.01)
*E03D 11/13* (2006.01)
*G16H 80/00* (2018.01)

(58) Field of Classification Search
USPC .............................................................. 4/420
See application file for complete search history.

(56) References Cited

U.S. PATENT DOCUMENTS

| | | | | |
|---|---|---|---|---|
| 11,119,091 | B2 * | 9/2021 | Sun | G01N 33/493 |
| 11,604,177 | B1 * | 3/2023 | Park | G06T 7/90 |
| 11,913,937 | B2 * | 2/2024 | Sun | G16H 30/40 |
| 2018/0085098 | A1 * | 3/2018 | Attar | G01J 3/10 |
| 2018/0303466 | A1 | 10/2018 | Kashyap et al. | |
| 2018/0372717 | A1 | 12/2018 | Tu et al. | |
| 2019/0369085 | A1 | 12/2019 | Tan et al. | |
| 2020/0187863 | A1 | 6/2020 | Tu et al. | |
| 2022/0395149 | A1 * | 12/2022 | Shimazu | A61B 5/207 |
| 2024/0090879 | A1 * | 3/2024 | Kanai | A61B 5/746 |

FOREIGN PATENT DOCUMENTS

| | | | |
|---|---|---|---|
| CN | 204228468 | U | 3/2015 |
| CN | 105804189 | A | 7/2016 |
| CN | 209074679 | U | 7/2019 |
| WO | 2012077933 | A2 | 6/2012 |

OTHER PUBLICATIONS

Chinese Office Action from Chinese Patent Application No. 2023052201629220, dated May 22, 2023, 13 pages. (including English summary).
Foreign Action other than Search Report on Taiwanese Appl. Ser. No. 108102151 dated Mar. 30, 2020. (4 pages).
Notice of Preliminary Rejection KR AppIn No. 2020052216880 dated Jul. 31, 2020 (5 pages).

* cited by examiner

METHOD AND DEVICE FOR AUTOMATICALLY TRACKING URINE

CROSS-REFERENCE TO RELATED PATENT APPLICATIONS

This application is a Continuation of U.S. patent application Ser. No. 17/402,184, filed Aug. 13, 2021, which is a Continuation of U.S. patent application Ser. No. 16/299,773, filed Mar. 12, 2019, which claims priority to and the benefit of Chinese Patent Application No. 201810205162.7, filed Mar. 13, 2018. The entire disclosure of the foregoing application, including the specification, drawings, claims, and abstract, is incorporated herein by reference in its entirety.

BACKGROUND

The present application relates generally to the field of urine detection, and more particularly, to a method and device of automatically tracking urine.

With the improvement of people's living standard, a smart toilet has gradually stepped into people's life. In addition to satisfying comfort requirements, the smart toilet is additionally provided with a health monitoring function that provides health data analysis through collecting a urine sample. However, using the urine collected from an inner surface of the toilet bowl for detection may have cross-contamination problems, which can affect the accuracy of the analysis of the health data. In order to avoid the cross-contamination problems affecting the accuracy of the health data analysis, the applicant's authorized patent 201610273915.9 discloses an automatic urine positioning method and device and a healthy smart toilet containing the same, in which it is pointed out that a non-contact temperature sensor driven by a stepping motor arranged on the left or right side wall of the toilet bowl can scan temperature in a mode of sector scanning within a certain angle range, and then the value X and/or Y in the coordinate (X, Y) of the position point of the urine in the toilet bowl can be calculated according to an angle and a tangent formula at the highest temperature.

According to the above said automatic urine positioning method and device and the healthy smart toilet containing the same, the cross contamination can be avoided through receiving the urine in the air. However, it has been found that there are still some shortcomings in the structure and the method in actual use, and since an optimal use effect may be difficult to achieve, the shortcomings can be summarized as set forth below.

(1) The structure and the positioning movement mode are complex, so that the stepping motor needs to drive the non-contract temperature sensor to move in a sector scanning mode.

(2) The coordinate of the position point of the urine needs to be calculated firstly, and then the urine-collection device will track and collect the urine, which has higher requirement on the installation of the whole device and the accuracy of the urine collecting and tracking members.

(3) Solely identifying the urine might be greatly influenced by environment and other factors.

Thus, it can be seen that the existing automatic urine positioning method and device and the healthy smart toilet containing the same still have inconvenience and defects in structure, method and use, and need to be further improved. How to create a method and device of automatically tracking urine with a simple structure and tracking movement mode, a higher accuracy, and capacity of avoiding cross contamination have become a target urgently needing to be improved in the current industry.

SUMMARY

The technical problem to be solved by the present invention is to provide a method and device of automatically tracking urine, which are simple in structure and tracking movement mode, relative higher in accuracy, and capable of avoiding cross contamination.

In order to solve the above technical problems, the present invention adopts the following technical solutions.

According to one aspect, the present invention provides a method of automatically tracking urine applicable to a toilet provided with an image sensor and a urine-collection device on an inner side wall, wherein a liquid-collection head of the urine-collection device is a collecting and tracking member, and is used for tracking and collecting the urine at the same time.

According to one example, the method comprises:

Step 1 ("S1"), which includes acquiring an image of an interior of a toilet bowl through an image sensor, wherein the image of the interior of the toilet bowl comprises an image of urine or an image simultaneously showing the urine and the collecting and tracking member;

Step 2 ("S2"), which includes identifying the urine or simultaneously identifying the urine and the collecting and tracking member through processing the image acquired in S1; and Step ("S3"), which includes implementing tracking movement to the urine by the collecting and tracking member in response to a result of the identification to the image acquired in S2.

Optionally, in S2, each pixel point in an acquired image can be compared with a threshold value set through an image characteristic of the urine to recognize the urine; or each pixel point in the acquired image can be compared with threshold values respectively set through image characteristics of the urine and the collecting and tracking member to recognize the urine and the collecting and tracking member.

Further, a background image can be firstly acquired before S1, where the background image is an image acquired when there is no urine nor the collecting and tracking member in the interior of the toilet bowl. Accordingly, in S2, the image can be processed to generate a difference image, where the difference image is a difference between the background image and the acquired image of the interior of the toilet bowl after the background image is acquired (e.g., the image captured in S1).

Further, in S2, binarization processing can be conducted on the difference image to generate a binary image; and a Hough transform can be conducted on the binary image in response to characteristic functions of the urine and the collecting and tracking member. For example, a column number of the urine and a column number of the collecting and tracking member can be identified according to a maximum value obtained from a Hough transform of two sets of characteristic functions.

Optionally, the method can further include Step 4 ("S4"), which includes repeating S1, S2, and S3 until the collecting and tracking member coincides with the urine in the image, and the collecting and tracking member stops moving.

Further, the characteristic function of the urine describes a vertical line, and the characteristic function of the collecting and tracking member describes a geometric curve related to a position and a shape of the collecting and tracking member.

According to another aspect, the present invention further provides a device of automatically tracking urine, which is a smart toilet, wherein an image sensor and a urine-collection device are installed on an inner side wall of the smart toilet, and a liquid-collection head of the urine-collection device is a collecting and tracking member, and is used for tracking and collecting the urine at the same time.

According to one example, the device of automatically tracking urine includes a memory, a processor, and a computer program that is stored in the memory and is executable on the processor, wherein the processor implements the above steps when (e.g., in response to) executing the computer program.

Optionally, the image sensor can be an infrared image sensor, a visible-light image sensor, or other suitable sensor.

Optionally, the image sensor can be installed on a left side wall or a right side wall of the smart toilet, and the urine-collection device is installed on the left side wall or the right side wall of the smart toilet. For example, the image sensor and the urine-collection device can be installed on opposite side walls.

Optionally, the image sensor can be installed on a front side wall or a rear side wall of the smart toilet, and the urine-collection device is installed on the front side wall or the rear side wall of the smart toilet. For example, one of the image sensor and the urine-collection device can be installed on the front side wall, and the other can be installed on the rear side wall.

Optionally, the collecting and tracking member can be provided with a color mark.

Optionally, the smart toilet can be replaced by a medical urine detection device.

Through the above technical solutions, the present invention provides at least the following advantages.

(1) The present invention relates to a method of automatically tracking urine based on image recognition, which uses the phenomenon that the urine, the urine-collection device, and the toilet have different image characteristics. The method employs the image sensor to collect the image of the interior of the toilet bowl, and recognizes the urine and the collecting and tracking member in the image to generate the motion function of the urine-collection device. The urine-collection device can automatically track the urine through the method above, so that the urine can be automatically tracked and collected by the urine-collection device when entering but not contacting the toilet, and thereby cross contamination of a urine sample is prevented and the accuracy of health data analysis is improved.

(2) When the collecting and tracking member of the urine-collection device coincides with the urine in the image, the urine-collection device stops moving. Through this method, a feedback control algorithm that simultaneously recognizes the urine and the collecting and tracking member is used, without calculating the specific position of the urine, thus the urine tracking accuracy by the collecting and tracking member is greatly improved, and the influence of the accuracy of the collecting and tracking member on urine tracking in the algorithm of solely identifying urine is removed. This method has higher accuracy and response speed.

(3) The difference image is used as an input of the control algorithm to eliminate the influences of the background difference and the sensor difference in the toilet on control.

(4) The device of tracking urine of the present invention uses the image sensor to acquire the position of the urine or the position information of the urine and the collecting and tracking member. Compared with a urine tracking device that moves in a sector scanning mode with the non-contact temperature sensor driven by the stepping motor, the device of tracking urine of the present invention has a simple structure and a simple tracking movement mode, a higher accuracy, and a faster response speed.

DETAILED DESCRIPTION

Figure 1:
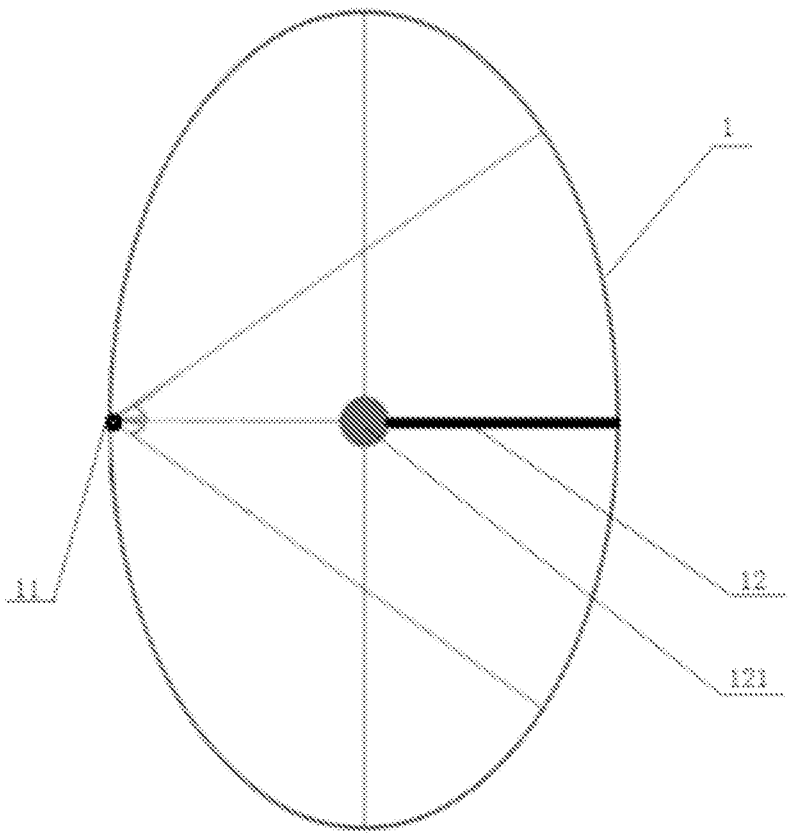
FIG. 1 is a structure diagram of a device of automatically tracking urine (toilet)

The present application relates to an automatic urine tracking device and method that employs image recognition, which, as shown in FIG. 1, is applicable to a toilet 1 provided with an image sensor 11 and a urine-collection device 12 on an inner side wall. Although the image sensor 11 and urine-collection device 12 are shown in FIG. 1 on opposing left and right side walls, they can be located on other portions of the toilet, such as opposing front and rear side walls. A liquid-collection head 121 of the urine-collection device 12 is a collecting and tracking member, and is used for collecting and tracking as well as identifying the urine at the same time. Several preferred automatic urine tracking methods are described in detail below.

Embodiment 1

Figure 2:
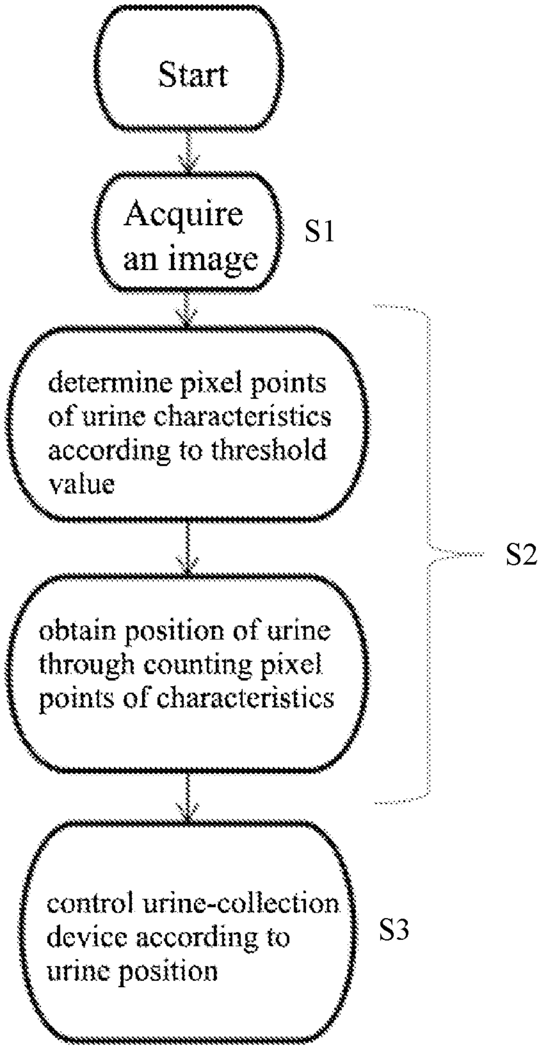
FIG. 2 is a flow chart of a method according to Embodiment 1.

FIG. 2 illustrates an example of an automatic urine tracking method that includes three steps. The method can be employed by a device for use with a toilet, such as the toilet 1, among other things.

Step 1 ("S1") involves acquiring an image of an interior of a toilet bowl through an image sensor, wherein the image of the interior of the toilet bowl comprises an image showing that there is urine in the toilet bowl.

Step 2 ("S2") involves recognizing the urine through image processing, which can include setting a threshold value according to an image characteristics of the urine; determining pixel points of the urine characteristics according to the threshold value; comparing each pixel of the image with the threshold value; and/or counting the pixels larger than the threshold value, wherein an area of pixels larger than the threshold value corresponds to the urine. S2 can involve calculating a position of the urine in the toilet bowl according to a position of the pixel with the largest value in the image.

Step 3 ("S3") involves controlling the urine-collection device according (e.g., in response) to the position of the urine, so as to make the collecting and tracking member implement urine tracking movement.

Embodiment 2

Figure 3:
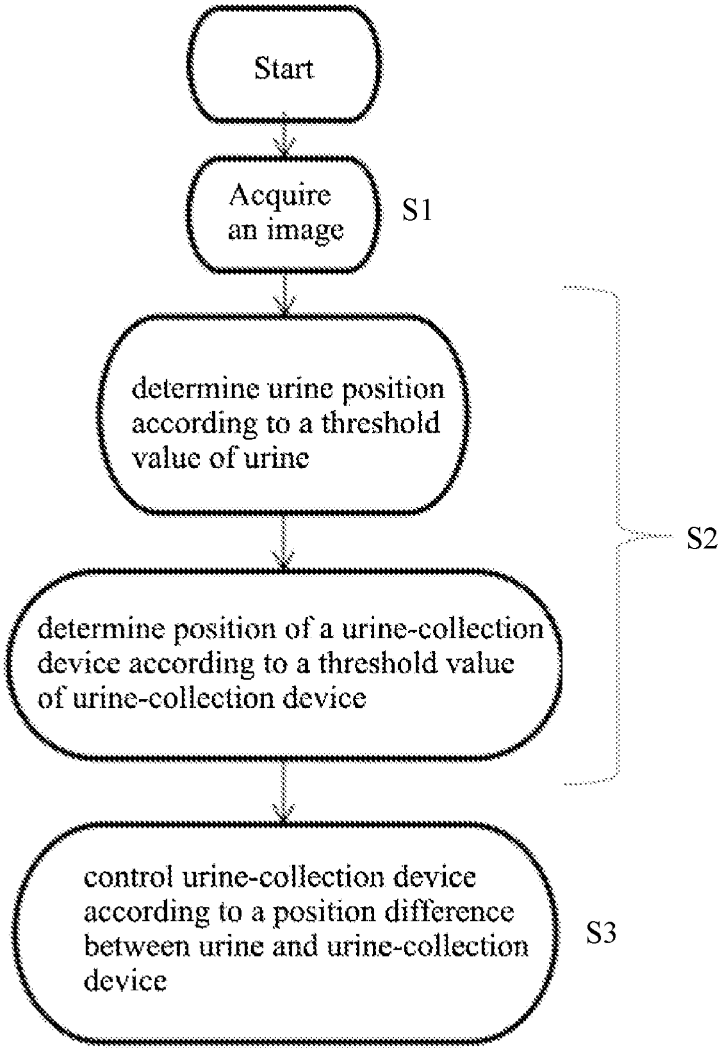
FIG. 3 is a flow chart of a method according to Embodiment 2.

FIG. 3 illustrates an example of an automatic urine tracking method that includes three steps. The method can be employed by a device for use with a toilet, such as the toilet 1, among other things.

Step 1 ("S1") involves acquiring an image of an interior of a toilet bowl through an image sensor, wherein the image of the interior of the toilet bowl comprises an image showing the urine and the collecting and tracking member.

Step 2 ("S2") involves identifying the urine and the collecting and tracking member through processing the image. More specifically, respectively setting threshold values for the urine and the collecting and tracking member, such as according to image characters of the urine and the collecting and tracking member; comparing the threshold values with each pixel point in the acquired image; counting the pixels larger than the threshold value of the collecting and tracking member, wherein an area of pixels larger than the threshold value corresponds to the collecting and tracking member; and/or counting the pixels which are larger than the threshold value of the urine and smaller than the threshold value of the urine-collection device, and an area of pixels within scope of the threshold value corresponds to the urine.

Step 3 ("S3") involves the collecting and tracking member moves towards the urine according to a location difference between the collecting and tracking member and the urine in the image.

Embodiment 3

Before S1 of Embodiment 1, the method further includes Step 0 ("S0").

S0 involves the image sensor firstly acquiring "n" groups of image data of the interior of the toilet bowl, then an average value of the image data is calculated (e.g., based on the "n" groups) as a background image and stored. The background image is an image showing no urine and no collecting and tracking member in the interior of the toilet bowl.

In S2, the image can be firstly processed to generate a difference image, and the difference image shows a difference between the acquired image of the interior of the toilet bowl and the background image after acquiring the background image.

Embodiment 4

Before S1 of Embodiment 2, the method further includes Step 0 ("S0").

S0 involves the image sensor firstly acquiring "n" groups of image data of an interior of the toilet bowl, then an average value of the image data is calculated (e.g., based on the "n" groups) as a background image and stored. The background image is an image showing no urine and no collecting and tracking member in the toilet bowl.

In S2, the image can be firstly processed to generate a difference image, and the difference image shows a difference between the acquired image of the interior of the toilet bowl and the background image after acquiring the background image.

Embodiment 5

In Embodiment 5, S2 of Embodiment 4 is replaced by subtracting background image data from the acquired image data every time to obtain a difference image. A binary image is generated, wherein the binary image is obtained by conducting binarization processing to the difference image; and the binarization processing method is to set a point in the image larger than the threshold value to 1 and a point in the image smaller than the threshold value to 0.

Hough transform is applied to (e.g., conducted on) the binary image according to characteristic functions of the urine and the collecting and tracking member, and column numbers corresponding to the urine and the collecting and tracking member respectively are identified according to a maximum value obtained from Hough transform of two sets of characteristic functions.

Figure 5:
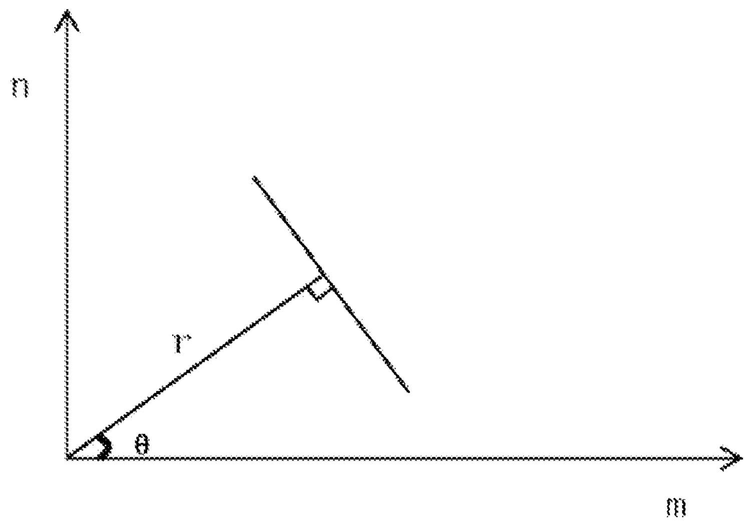
FIG. 5 is a principle diagram of a Hough transform.

As shown in FIG. 5, according to the principle of Hough transform, a characteristic equation of discrete points through which a line in the image passes is:

$$r=m*\cos(\theta)+n*\sin(\theta)$$

where r is a vertical distance from ordinate origin to the line, and θ is an included angle between r and a m-axis. That is, r is at the angle θ from the m-axis and an angle 90−θ from the n-axis, where the origin is the intersection of the m-axis and n-axis. FIG. 5 shows r intersecting the origin.

The characteristic function of the urine in the image describes a vertical line, and an angle θ of the characteristic equation of the urine is 0 degree.

An r value corresponding to all characteristic pixels of the urine is calculated and the number of occurrences of the same r value is counted. The r value with the most occurrences is the column number where the urine is located.

Figure 6:
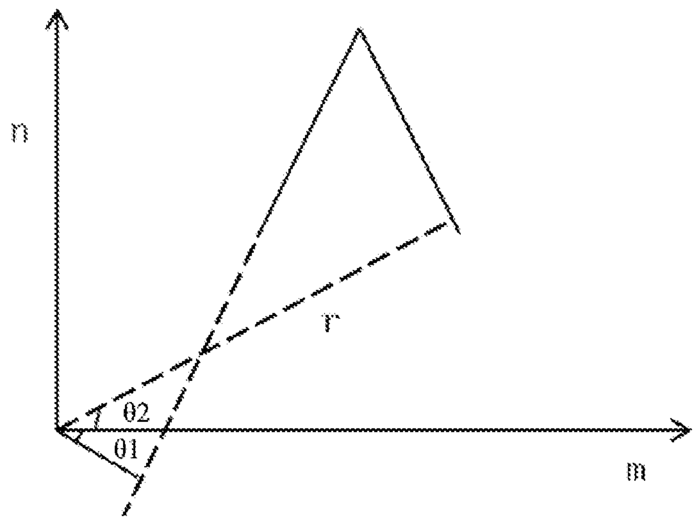
FIG. 6 is a principle diagram of a Hough transform of a urine-collection device.

It can be determined from FIG. 6 that a range of the angle θ in the characteristic equation of the urine-collection device is [θ1, θ2], the angle θ is divided into k parts, the r value of the characteristic pixel of the collecting and tracking member of the urine-collection device is calculated, and the number of occurrences of all r values is counted. The line corresponding to the r value with the most occurrences refers to the collecting and tracking member of the urine-collection device.

S3 is as follows: according to the location difference between the collecting and tracking member of the urine-collection device and the urine in the difference image, the urine-collection device moves towards the urine, specifically, according to a column difference ek between the recognized urine and the collecting and tracking member of the urine-collection device in the image, PI control (e.g., proportional-integral control) is conducted to the urine-collection device, and a control function is:

$$u(k)=Kp*ek+Ki*ek+u(k-1)$$

where u(k) is the $k^{th}$ output of the urine-collection device, u(k−1) is the $(k-1)^{th}$ output, Kp is a proportional coefficient, Ki is an integral coefficient, and ek is the $k^{th}$ difference.

Embodiment 6

Figure 4:
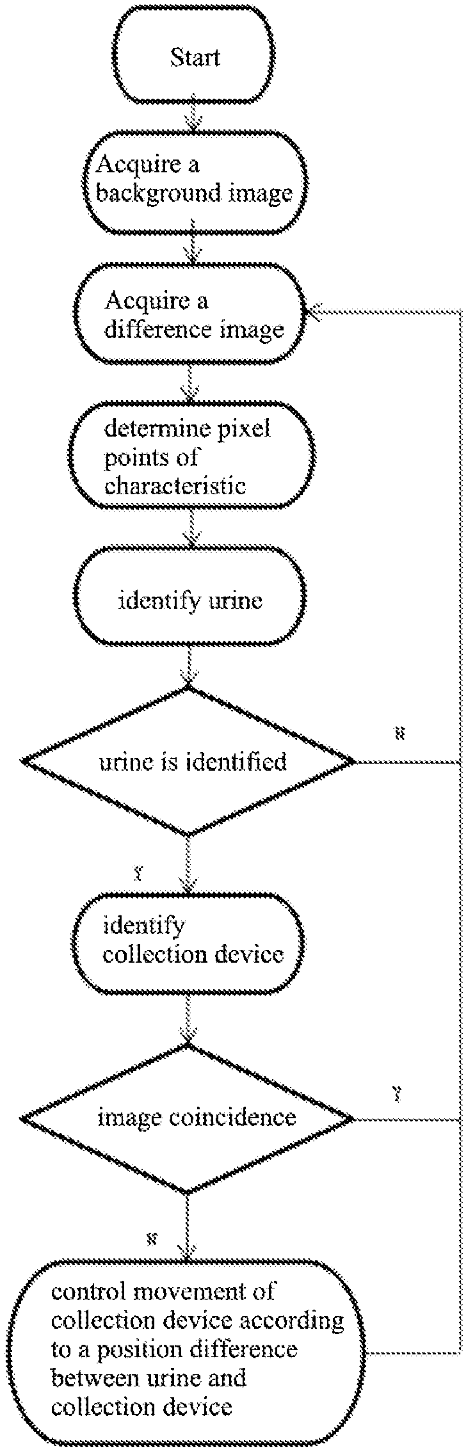
FIG. 4 is a flow chart of a method according to Embodiment 6.

On the basis of any one of the above embodiments (e.g., Embodiments 2, 4 and 5), a Step 4 ("S4") can be added, where S4 involves repeating S1, S2, and S3 until the collecting and tracking member coincides with the urine in the image, and the collecting and tracking member stops moving. FIG. 4 shows an example of such a method.

The present application further provides a device of automatically tracking urine, which is configured for use in a smart toilet. Referring back to FIG. 1, each of the image sensor 11 and the urine-collection device 12 is installed on an inner side wall of the smart toilet 1, and a liquid-collection head 121 of the urine-collection device 12 is configured as a collecting and tracking member, and is used for tracking and collecting the urine at the same time. The device of automatically tracking urine can also include a memory, a processor, and a computer program stored in the memory and executable on the processor, where the processor implements the steps of a method according to any of Embodiments 1-6 when executing the computer program.

The above said device of automatically tracking urine in a toilet can automatically track the urine based on image recognition. By using a phenomenon that the urine, the urine-collection device, and the toilet have different image characteristics, an image sensor is used to collect an image of an interior of the toilet bowl, and the urine and the collecting and tracking member are recognized from the image to generate a motion function of the urine-collection device. The urine-collection device can automatically track the urine through a method described above, so that the urine is automatically tracked and collected by the urine-collection device when entering but not contacting the toilet bowl. That is, the urine collection device tracks the urine within the bowl of the toilet and collects a sample of the urine prior to the urine contacting the bowl. Thereby, cross contamination of the urine sample can be prevented, and the accuracy of health data analysis is improved.

When the collecting and tracking member of the urine-collection device coincides with the urine in the image, the urine-collection device is configured to stop moving. Through this method, a feedback control algorithm is used for simultaneously identifying the urine and the tracking member, without having to calculate the specific position of the urine. Thus, the accuracy of tracking urine by the collecting and tracking member is greatly improved, and the influence of the accuracy of the tracking member on tracking urine related in the algorithm of solely identifying the urine is removed. This method has higher accuracy and response speed.

As a non-limiting example, the image sensor includes an infrared image sensor and/or a visible-light image sensor.

In at least one embodiment, the image sensor is arranged on the left side of the toilet bowl, and the urine-collection device is arranged on the right side of the toilet bowl. However, the present invention is not limited by the said installation method and/or structure, and those skilled in the art may understand that positions of the image sensor and the urine-collection device may also be interchanged, or both of the image sensor and the urine-collection device can be located on the left side or the right side of an inner wall of the toilet bowl, or the image sensor and the urine-collection device may be arranged on a front side or a back side of the inner wall of the toilet bowl. Alternatively, two sets of the urine-collection devices and the image sensors may be arranged (the first set of the urine-collection device and the image sensor are arranged on the left side or the right side of the toilet bowl, and the second set of the urine-collection device and the image sensor are arranged on the front side or the back side of the toilet bowl, which have higher matching accuracy, and the requirement on a liquid collection range of the tracking member of the urine-collection device will be greatly reduced).

Optionally, in order to cooperate with the image sensor to acquire a difference image, the collecting and tracking member of the urine-collection device can be provided with a color mark and/or other marks that can facilitate image recognition during use. A shape of the collecting and tracking member may also be any geometric shape such as a circle, a triangle, a square, etc.

The embodiments above are described with an example of a smart toilet. Certainly, those skilled in the art may understand that, in order to achieve the purpose of automatically tracking and detecting the urine, the above device does not need to be limited to the toilet, and may also be used in hospital. For example, the above method and device are also used in a container of a medical urine detection device in the hospital, and the purpose may be achieved by only replacing the container of the medical urine detection device with the toilet.

In conclusion, the urine-collection device may automatically track the urine through a disclosed method based on image recognition according to the present invention, so that the urine may be automatically tracked and collected by the urine-collection device when entering or passing through the toilet bowl, but prior to contacting the toilet bowl. In this way, cross contamination of the urine sample is prevented, and the accuracy of health data analysis is improved. Especially, motion control is conducted according to whether or not the collecting and tracking member of the urine-collection device is coincident with the urine in the image, without having to calculate (e.g., without calculating) the specific position of the urine. Thus, the accuracy of tracking urine by the collecting and tracking member is greatly improved, and the influence of the accuracy of the collecting and tracking member on tracking urine in the algorithm of solely identifying the urine is removed. The method has higher accuracy and response speed, and is suitable for popularization and application.

The foregoing is merely preferred embodiments of the present invention without any limitation on the present invention in any form, and the simple amendments, equivalent changes or modifications made by those skilled in the art using the technical contents disclosed shall all fall within the protection scope of the present invention.

I claim:

1. A method of tracking urine in a toilet bowl, the method comprising:

generating a background image of the toilet bowl;

acquiring an image of the toilet bowl and the urine using an image sensor;

calculating a difference image based on a difference between the acquired image and the background image; and processing the difference image to identify a location of the urine, wherein the image sensor is located at a front wall or a rear wall of the toilet bowl.

2. The method of claim 1, further comprising:

conducting binarization of the difference image based on a threshold value.

3. The method of claim 1, wherein generating the background image comprises:

acquiring “n” groups of image data of the toilet bowl using the image sensor; and calculating an average value of the “n” groups of image data to calculate the background image.

4. The method of claim 1, wherein calculating the difference image comprises:

comparing each pixel in the acquired image with a threshold value set through an image characteristic of urine to identify the urine.

5. The method of claim 4, wherein calculating the difference image comprises:

counting pixels that are larger than the threshold value, wherein an area of pixels larger than the threshold value corresponds to urine.

6. The method of claim 5, wherein calculating the difference image comprises:

calculating a position of the urine in the toilet bowl according to a position of the pixel with a largest value in the acquired image.

7. The method of claim 1, wherein the image sensor is located at a side wall of the toilet bowl.

8. A method of tracking urine in a toilet bowl, the method comprising:

acquiring a first image of the toilet bowl using an image sensor;

acquiring a second image of the toilet bowl and the urine using the image sensor;

calculating a difference image for a difference between the second image and the first image;

conducting binarization of the difference image based on a threshold value; and processing the difference image to identify a location of the urine.

9. The method of claim 8, wherein acquiring the first image comprises:

acquiring "n" groups of image data of the toilet bowl using the image sensor; and calculating an average value of the "n" groups of image data to calculate the first image.

10. The method of claim 8, wherein calculating the difference image comprises:

comparing each pixel in the acquired image with a threshold value set through an image characteristic of urine to identify the urine.

11. The method of claim 10, wherein calculating the difference image comprises:

counting pixels that are larger than the threshold value, wherein an area of pixels larger than the threshold value corresponds to urine.

12. The method of claim 11, wherein calculating the difference image comprises:

calculating a position of the urine in the toilet bowl according to a position of the pixel with a largest value in the second image.

13. The method of claim 8, wherein the image sensor is located at a side wall of the toilet bowl.

14. The method of claim 8, wherein the image sensor is located at a front wall or a rear wall of the toilet bowl.

15. A urine detection device for a toilet bowl, the urine detection device comprising:

an image sensor;

a memory;

a processor;

and a computer program, wherein the computer program is stored in the memory and is executable on the processor, and wherein the processor implements:

acquiring a first image of the toilet bowl;

acquiring a second image of the toilet bowl and the urine using the image sensor; and calculating a difference image for a difference between the second image and the first image, wherein the memory stores the first image and the first image includes no urine.

16. The urine detection device of claim 15, wherein the processor implements:

processing the difference image to identify a location of the urine.

17. The urine detection device of claim 15, further comprising:

a urine collection device installed on a different wall of the toilet bowl than the image sensor.

* * * * *